(12) United States Patent
Zacco

(10) Patent No.: US 7,004,172 B1
(45) Date of Patent: *Feb. 28, 2006

(54) MOUTHPIECE FOR REDUCING SNORING

(76) Inventor: Christopher Zacco, 1217 SE. 17th St., Ocala, FL (US) 34471

( * ) Notice: Subject to any disclaimer, the term of this patent is extended or adjusted under 35 U.S.C. 154(b) by 0 days.

This patent is subject to a terminal disclaimer.

(21) Appl. No.: 10/862,948

(22) Filed: Jun. 8, 2004

Related U.S. Application Data

(63) Continuation-in-part of application No. 10/657,327, filed on Sep. 8, 2003, which is a continuation-in-part of application No. 10/289,588, filed on Nov. 7, 2002, now Pat. No. 6,619,290.

(51) Int. Cl.
*A61F 5/56* (2006.01)
(52) U.S. Cl. ....................................... 128/848
(58) Field of Classification Search ................ 128/859, 128/848, 861, 862; 433/1, 6
See application file for complete search history.

(56) References Cited

U.S. PATENT DOCUMENTS

| 3,871,370 | A | * | 3/1975 | McDonald | .................. 128/860 |
| 5,117,816 | A | * | 6/1992 | Shapiro et al. | ........ 128/200.24 |
| 5,636,379 | A | * | 6/1997 | Williams | ........................ 2/455 |

* cited by examiner

*Primary Examiner*—Henry Bennett
*Assistant Examiner*—Camtu Nguyen
(74) *Attorney, Agent, or Firm*—Allen, Dyer, Doppelt, Milbrath & Gilchrist, P.A.

(57) ABSTRACT

A mouthpiece and method for reducing snoring comprise a mouthpiece body of a thermoplastic material having a shape generally complementary to the person's dental arch, including a posterior end having two spaced apart members positioned toward the back of the person's dental arch when properly worn, and an anterior end having an airway opening therethrough, the anterior end positioned when properly worn to support the person's lips spaced apart so that air flows through the airway opening; and a substantially rigid protective mold of a thermostable material, the protective mold protecting at least a periphery of the mouthpiece body.

15 Claims, 8 Drawing Sheets

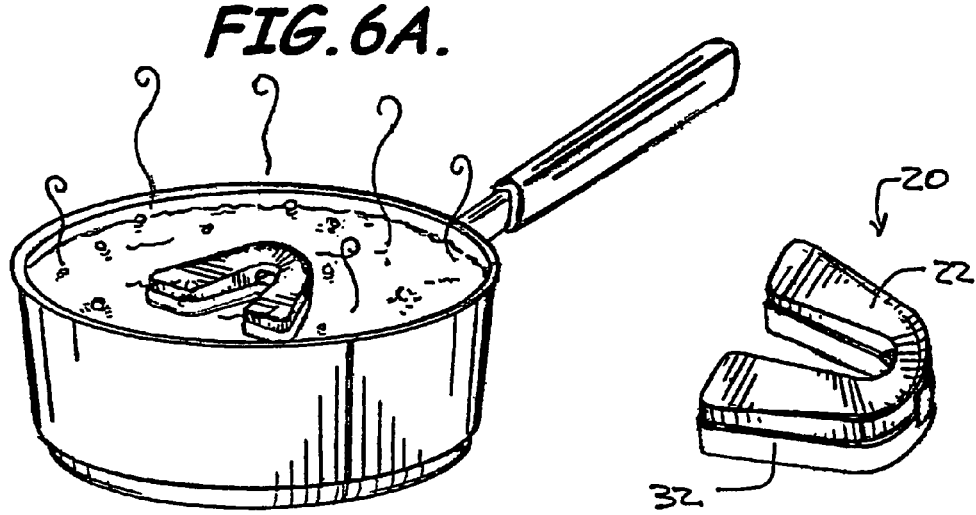
FIG.6A.
FIG.6B.
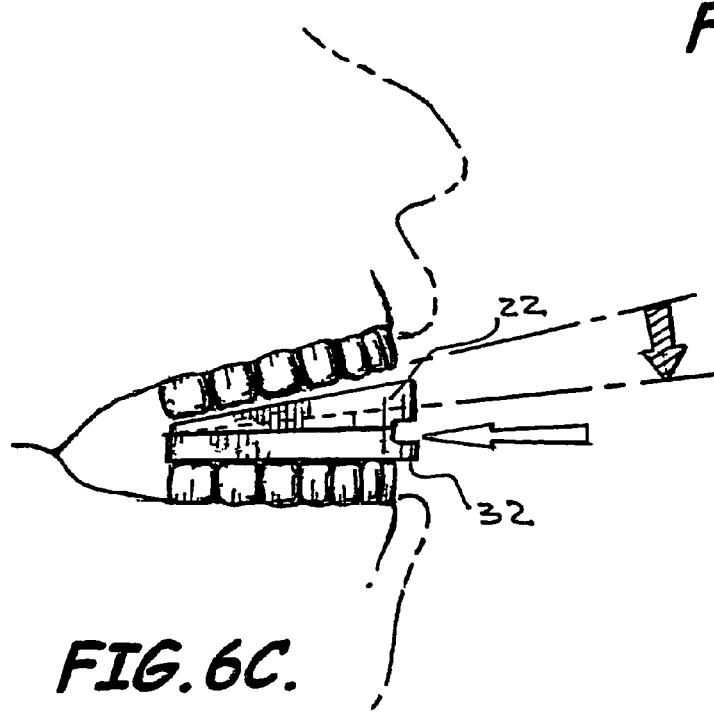
FIG.6C.

MOUTHPIECE FOR REDUCING SNORING

RELATED APPLICATION

This application is a continuation-in-part of and claims priority from co-pending U.S. application Ser. No. 10/657,327 which was filed on Sep. 8, 2003, and which was a continuation-in-part of U.S. application Ser. No. 10/289,588, filed on Nov. 7, 2002, now U.S. Pat. No. 6,619,290, all of which are incorporated herein by reference in their entirety.

FIELD OF THE INVENTION

The present invention relates to the field of sleep aids and, more particularly, to a mouthpiece for helping to reduce snoring in a wearer, the mouthpiece having a thermoplastic portion and a thermostable portion.

BACKGROUND OF THE INVENTION

It is well known that many people snore when asleep. Snoring is an unconscious activity which is often not even noticed by the person who snores, but is typically quite bothersome to those sleeping nearby.

Medical references define snoring as a rough, rattling, inspiratory noise generally produced by vibration of the pendulous palate, or sometimes by the vocal cords, during sleep. Snoring may be produced as a rale, especially a whistling or sonorous rale produced in the larger bronchi or the trachea. This condition is caused by some narrowing of the upper airway passages, such that when the person is asleep, the airflow is somewhat obstructed and must be forced.

SUMMARY OF THE INVENTION

With the foregoing in mind, the present invention advantageously provides a thermoplastic mouthpiece which may be custom fitted directly by the user to conform to his or her natural dental arch. The mouthpiece is reusable, but intended to be disposable at the user's discretion. In a preferred embodiment, the mouthpiece includes a body of thermoplastic material having a shape generally complementary to the person's dental arch. The mouthpiece body includes a posterior end having two spaced apart members positioned toward the back of the person's dental arch when properly worn, and an anterior end having an airway opening therethrough, the anterior end positioned when properly worn to support the person's lips spaced apart so that air flows through the airway opening. The airway may preferably comprise thermostable material, so as to aid in maintaining the shape of the airway while the mouthpiece is heated. A plate member comprises material which extends between the two spaced apart members from approximately the posterior end to the anterior end of the mouthpiece body. The plate preferably comprises thermostable material, but may optionally comprise thermoplastic material. A substantially rigid, protective mold of a thermostable material forms a portion of the mouthpiece body so that the mold protects at least a periphery of the mouthpiece body.

In another preferred embodiment, the invention also includes a removable plug inserted into the airway opening to help support the opening during heating of the mouthpiece and during the imprinting of teeth by the user. Additionally, this removable plug may be used as a handle when inserted in the airway opening of the mouthpiece, for the user to pick up the mouthpiece during heating and during use.

In use, the wearer heats the mouthpiece until its thermoplastic portion softens sufficiently for biting down on the mouthpiece to imprint the wearer's teeth pattern thereon. The mouthpiece includes a protective mold along a lower surface, the mold optionally extending upwardly to also protect lateral surfaces of the mouthpiece. The protective mold is thermostable and is separable from the mouthpiece body, but may also be an integral unitary piece of the mouthpiece together with the thermoplastic portion, thus the mold does not soften when the mouthpiece is heated, which is preferably accomplished by placing the mouthpiece in a hot water bath for a few minutes. When the thermoplastic portion of the mouthpiece softens and cools a bit, the wearer inserts the device into the mouth such that it is substantially aligned with the dental arch, and gently bites down on the mouthpiece to thereon make an impression with his teeth. Of course, along the lower surface of the mouthpiece the thermostable protective mold prevents the teeth from leaving an imprint. This helps maintain a proper angle of inclination between the spaced apart lower and upper surfaces of the mouthpiece, and it is this angle which is most helpful in keeping the wearer's lips apart during sleep, and thus help the airway to stay open. Once the mouthpiece has been imprinted, the wearer inserts the mouthpiece into his mouth when preparing for sleep and removes the airway opening plug to provide unobstructed passage of air. In an alternative embodiment of the invention useful as an aid in reducing teeth grinding during sleep, the mouthpiece may lack an airway opening.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 6 illustrates various aspects of a method of the present invention;

DETAILED DESCRIPTION OF THE PREFERRED EMBODIMENT

The present invention will now be described more fully hereinafter with reference to the accompanying drawings, in which preferred embodiments of the invention are shown.

This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

Figure 1:
FIG. 1 shows an overall view of a sleeper wearing the mouthpiece according to an embodiment of the present invention.
Figure 2:
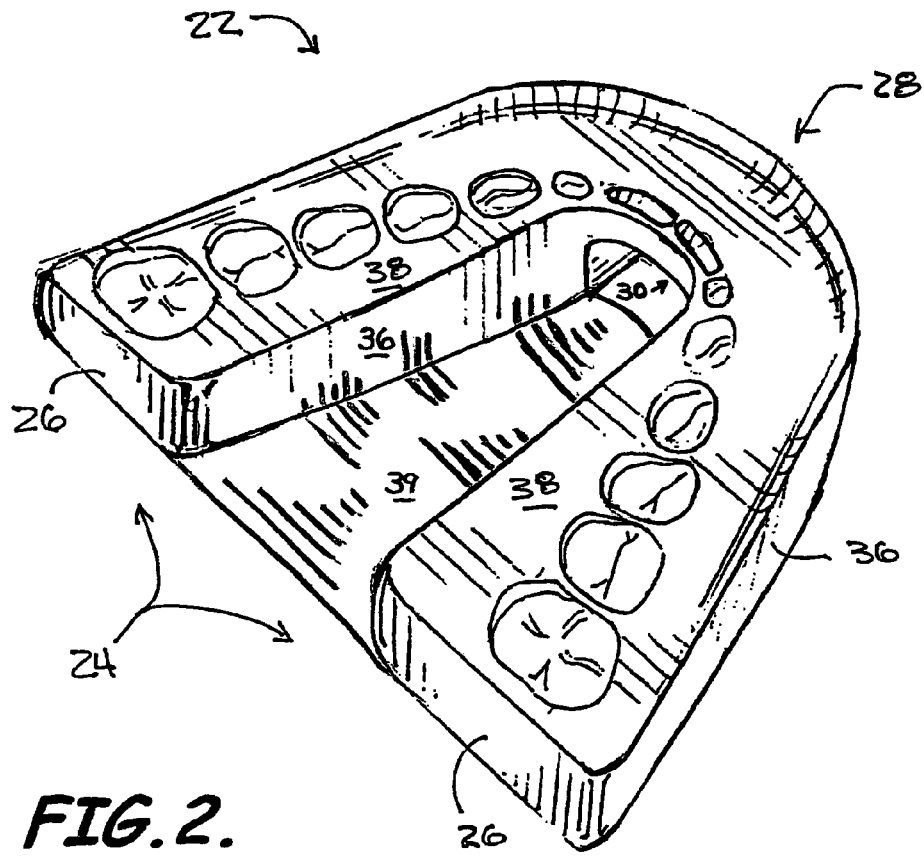
FIG. 2 is a top perspective view of the mouthpiece of FIG. 1.
Figure 3:
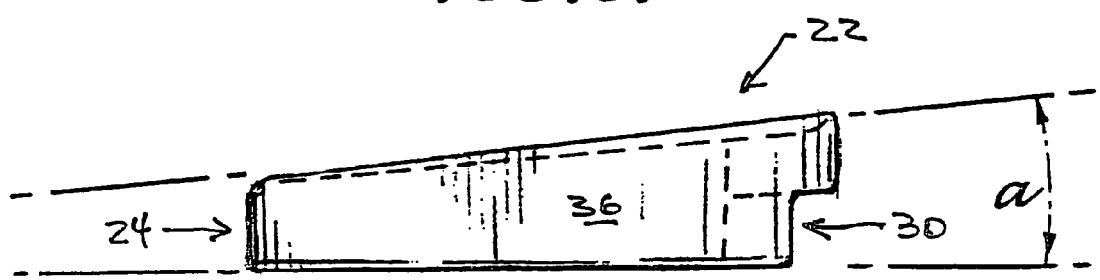
FIG. 3 shows a side elevation of the present mouthpiece.
Figure 4:
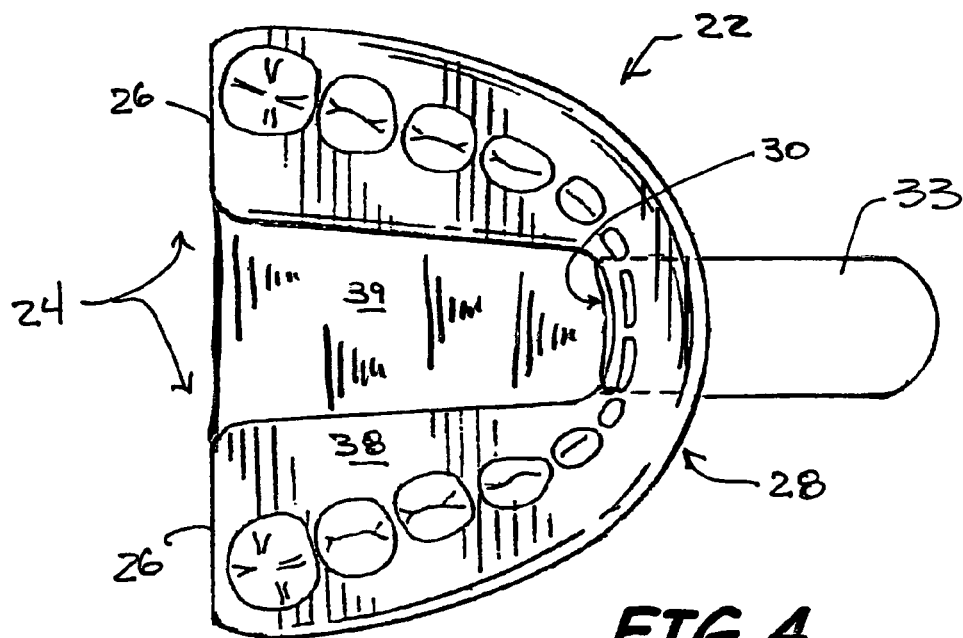
FIG. 4 is a top plan view of the inventive mouthpiece.
Figure 5:
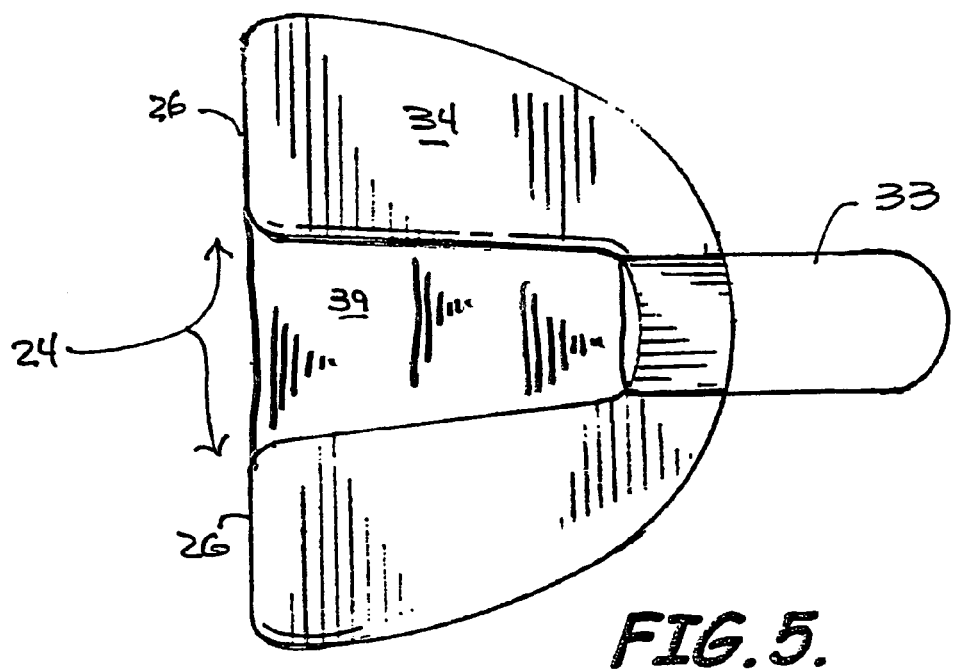
FIG. 5 is a bottom plan view of the mouthpiece of FIG. 4.
Figure 7:
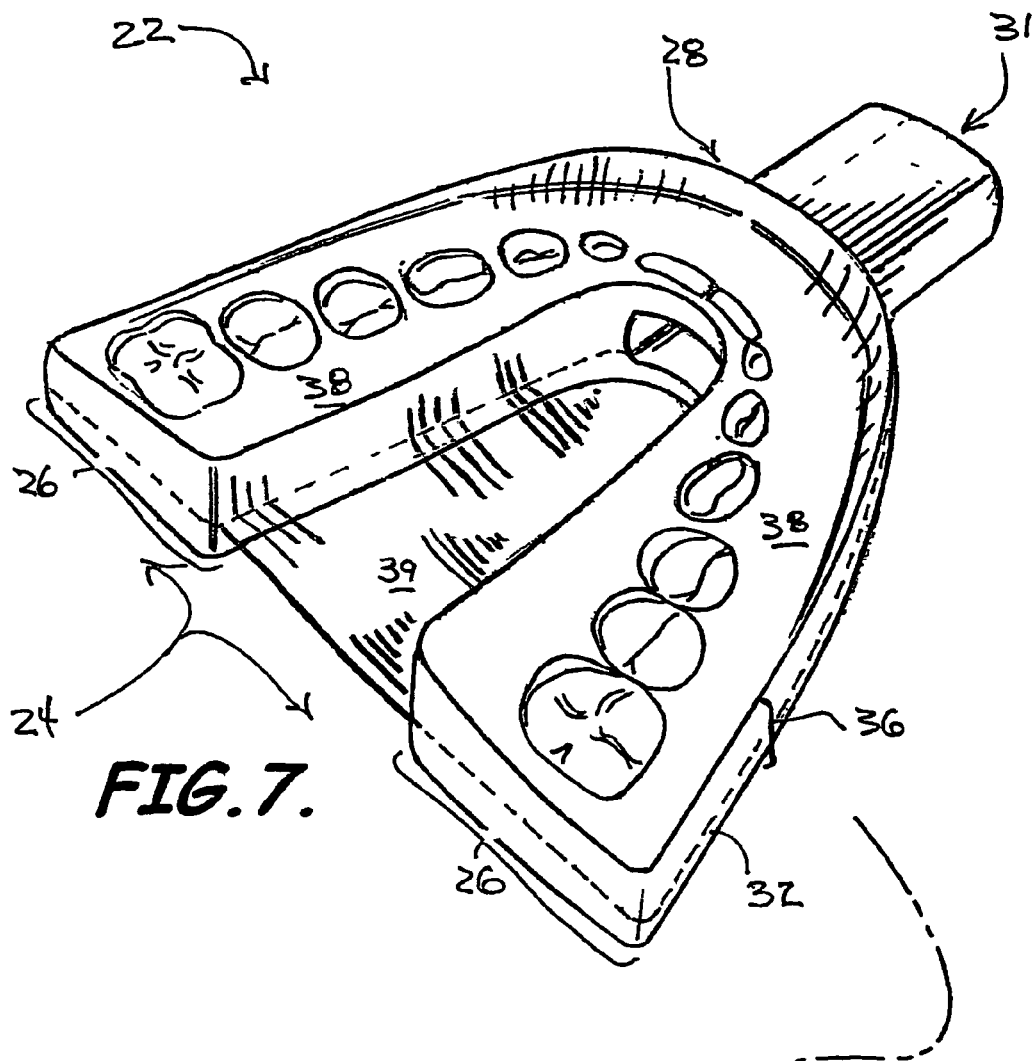
FIG. 7 shows another embodiment of the present mouthpiece.
Figure 8:
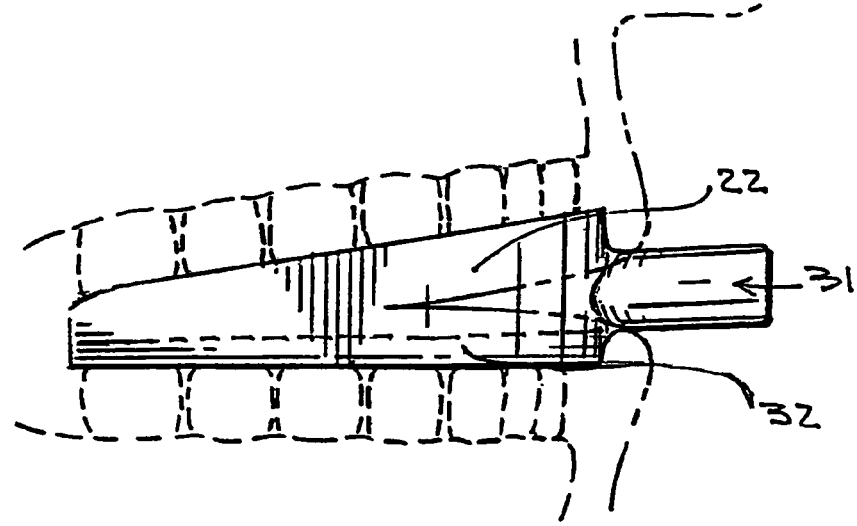
FIG. 8 is a cutaway lateral view showing the mouthpiece of FIG. 7 as worn by a user.
Figure 9:
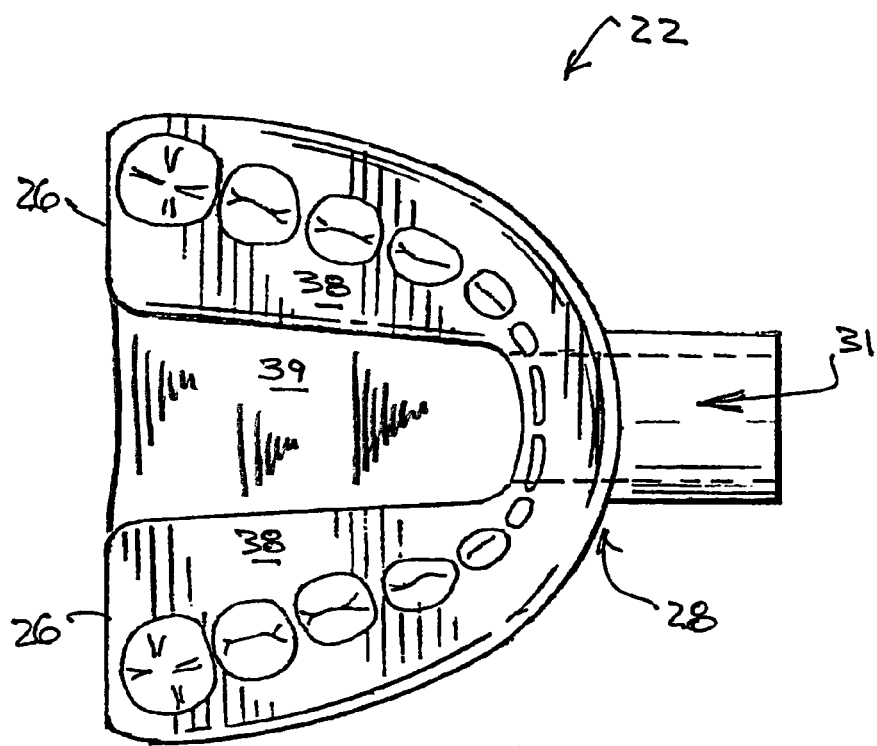
FIG. 9 is a top plan view of the mouthpiece of FIG. 7.
Figure 10:
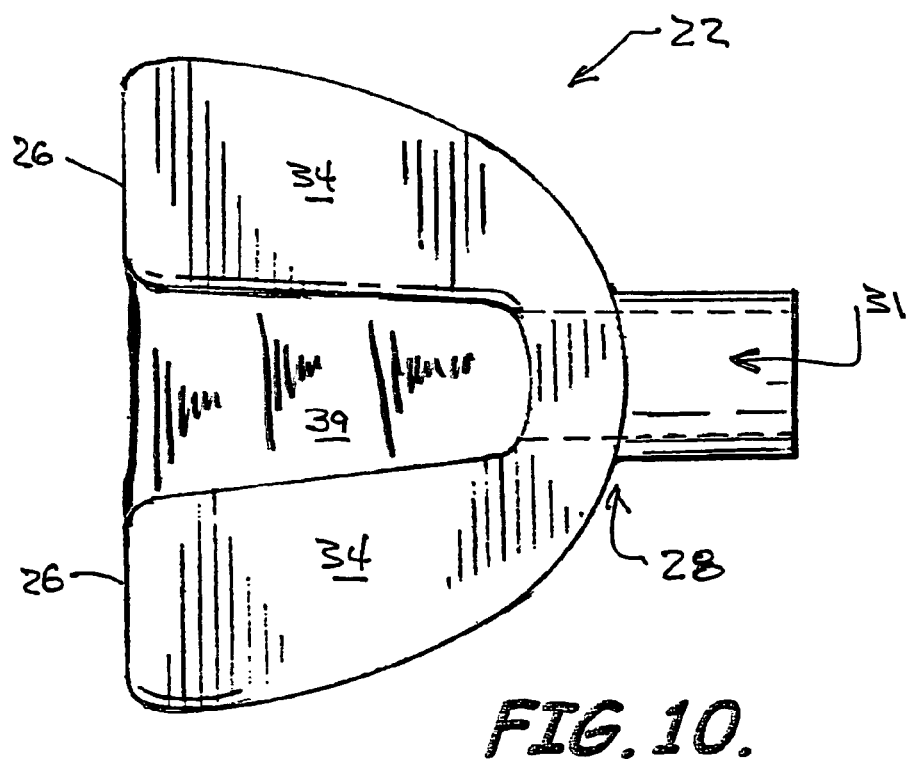
FIG. 10 is a bottom plan view of the mouthpiece of FIG. 9.

FIGS. 1–12 illustrate the various aspects of the inventive mouthpiece herein described. The invention discloses a mouthpiece 20 for use by a person during sleep to aid in reducing snoring. The mouthpiece 20 comprises a mouthpiece body 22 made of a thermoplastic material having a shape generally complementary to the person's dental arch, including a posterior end 24 having two spaced apart members 26 positioned toward the back of the person's dental arch when properly worn, and an anterior end 28 having an airway opening 30 therethrough, the anterior end positioned when properly worn to support the person's lips spaced apart, as shown in FIG. 1, so that air flows through the airway opening. As noted above, however, in an alternative embodiment the present mouthpiece may be provided without an airway opening. This alternate embodiment is intended to aid in reducing teeth grinding. The mouthpiece 20 additionally includes a substantially rigid portion or protective mold 32 made of a thermostable material, the protective mold being complementary to the mouthpiece body 22 so that the mold protects at least lower surfaces 34 and preferably also lateral 36 surfaces of the mouthpiece body, as illustrated in FIGS. 6A–D. The mold may be a discrete piece separable from the mouthpiece, or may be an integral, unitary non-separable piece therewith. Additionally, as shown in FIGS. 4 and 5, the present mouthpiece includes a removable plug 33 inserted in airway opening 30 and protruding therefrom. Plug 33 serves at least two purposes. First, it provides support so as to protect the integrity of airway opening 30 during heating of the mouthpiece and while the user bites down on the mouthpiece to imprint the teeth thereon. Second, the removable plug 33 serves as a handle by which the user may pick up the mouthpiece, which is useful in placing and removing the mouthpiece in a hot water bath, and in inserting the mouthpiece in the mouth. Plug 33 may be discarded by the user after imprinting teeth on the mouthpiece, or may be replaced in the airway opening 30 after use of the mouthpiece for continued use as a handle.

Figure 11:
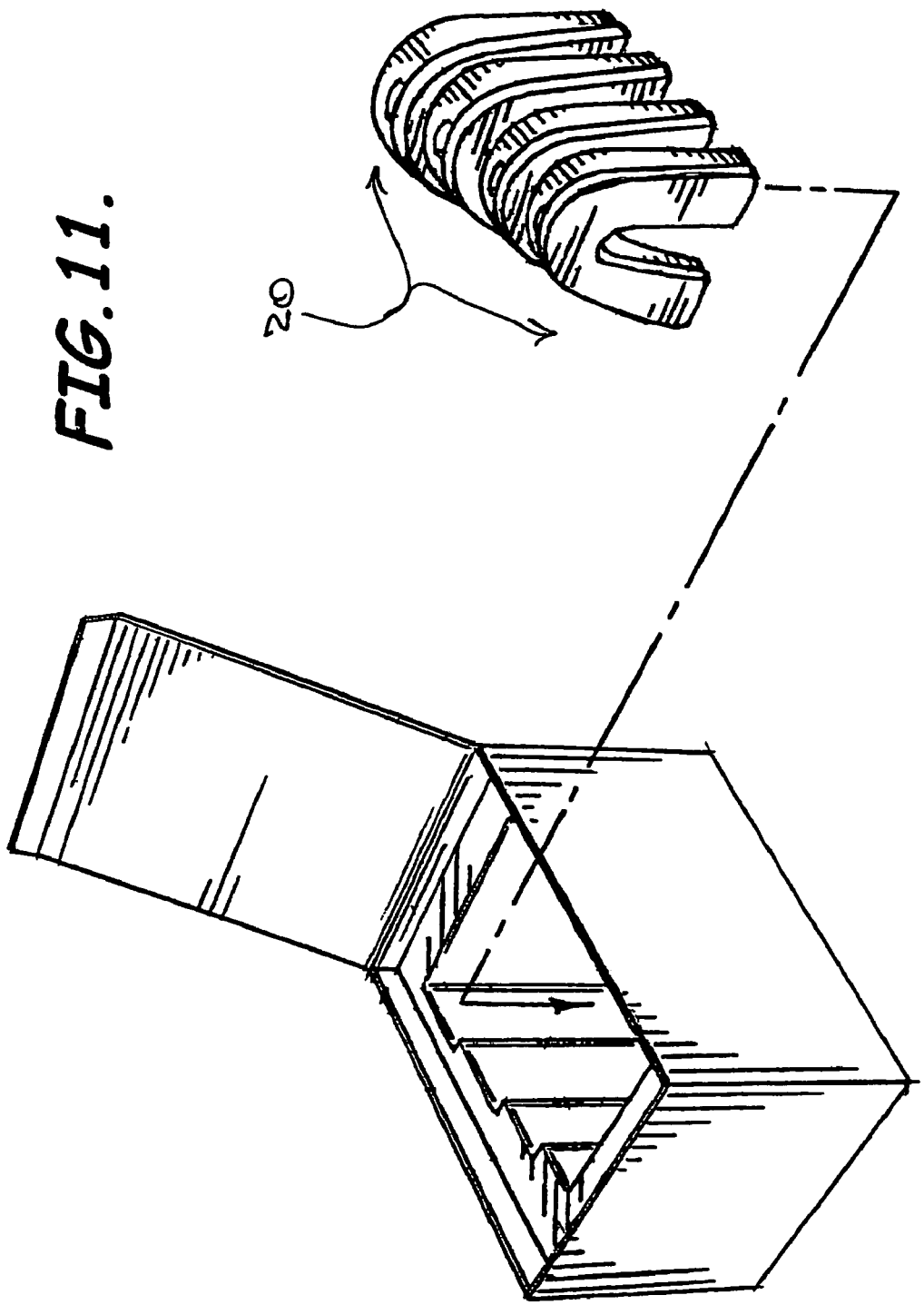
FIG. 11 illustrates a kit containing several of the mouthpieces of FIG. 1 as might be offered at retail.

The present mouthpiece 20 is preferably provided for retail sale in at least three general sizes, small, medium, and large, to custom fit a wide range persons having differently sized mouths. A typical retail kit 21 for sale of the mouthpiece 20 is shown in FIG. 11. Partly for the purpose of custom fitting, the mouthpiece body 22 has a lower surface 34 and an upper surface 38 spaced apart therefrom at an angle "α" which increases from the posterior end 24 to the anterior end 28 of the mouthpiece body. As best shown in FIG. 3, and also in FIGS. 6C, and 8, the angle of inclination "α" between the upper 38 and lower 34 surfaces of the mouthpiece body 22 is of importance in keeping the wearer's mouth and lips sufficiently open to allow unimpeded airflow through the anterior airway opening 30. An angle "α" of from about 10° to 20° has been found preferable, depending on the anterior-posterior overall length of the mouthpiece, which will somewhat vary from small to medium to large mouthpieces. Those skilled in the art will recognize, however, that angle "α" may be changed according to the size of the wearer's mouth, and that the range indicated above is given solely for purposes of illustration and not for limiting the invention.

Another embodiment of the present invention is shown in FIGS. 7–10, wherein the mouthpiece body 22 further comprises a tubular airway opening 31 extending outwardly from the anterior end airway opening 30. This embodiment of the mouthpiece body, best shown in use in FIG. 8, would be particularly useful for wearers having large, heavy, or especially protruding lips which might extend over the anterior end of the first embodiment of the mouthpiece as shown in FIGS. 1–6. The skilled will readily understand that it is important to keep the wearer's lips sufficiently spaced apart to maintain the proper function of the airway opening 30 at the anterior end of the mouthpiece.

A preferred embodiment of the present invention includes the mouthpiece described above, but also including a plate member comprising material extending between said two spaced apart members from approximately the posterior end to the anterior end of said mouthpiece body. This embodiment is particularly illustrated in FIGS. 2, 4–5, 7, 9 and 10, wherein plate member 39 is shown. The plate member is useful in preventing the tongue from interfering with the airway while a person sleeps with the mouthpiece in place in the mouth. In this and other embodiments of the invention, the protective mold may be either integral, that is, one piece with the mouthpiece, or may be separable therefrom. Additionally, plate member 39 may optionally comprise thermostable or thermoplastic material. Moreover, airway opening 30 may also comprise either thermoplastic material, but preferably comprises thermostable material, so as to aid in maintaining the shape of the airway opening while the mouthpiece is heated and/or imprinted by the user.

Figure 12:
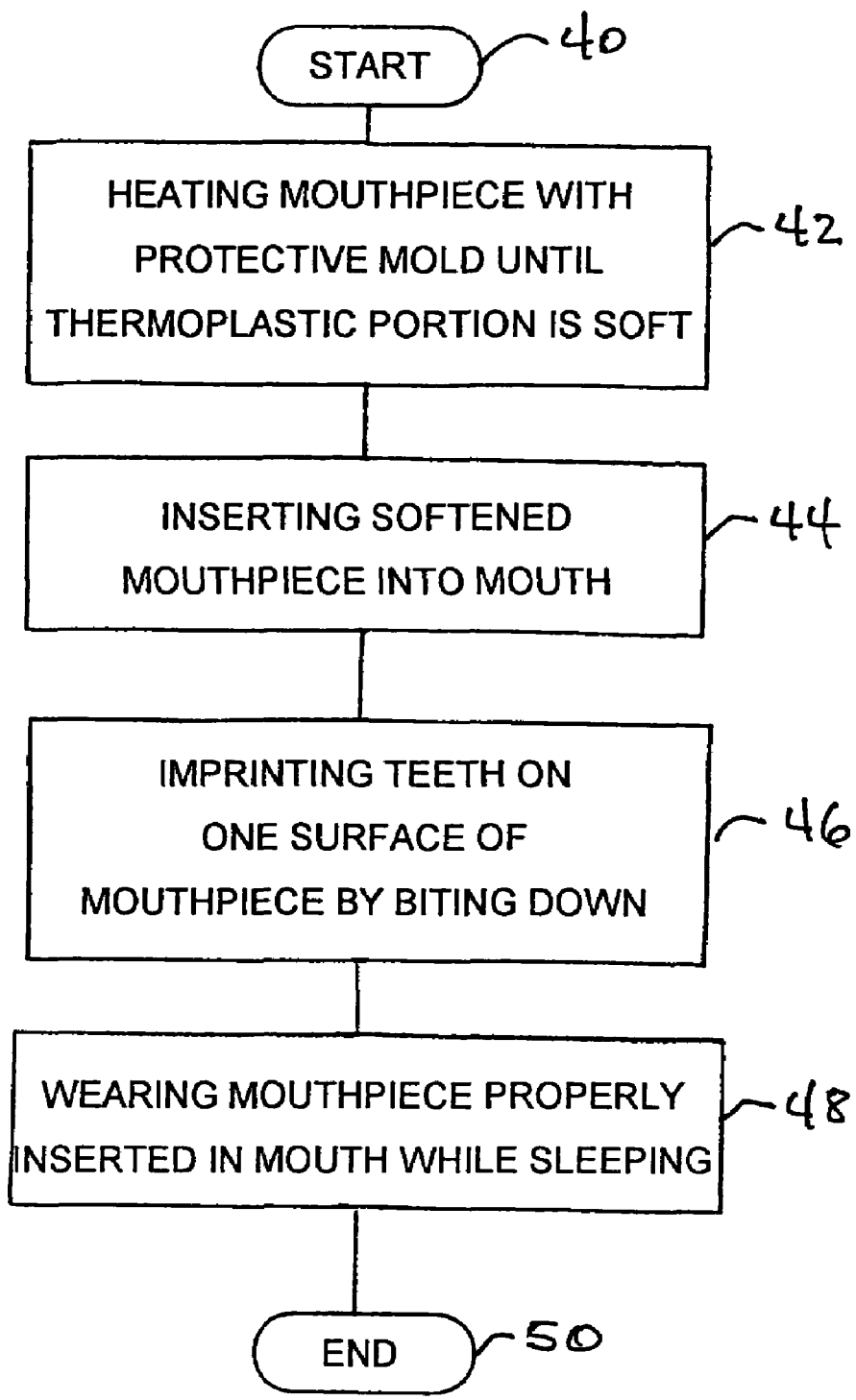
FIG. 12 shows a method of the invention of FIG. 1.

Method aspects of the present mouthpiece invention are shown in FIG. 6 and FIG. 12, and include a method of reducing snoring during sleep. As shown in the block diagram of FIG. 12, the method starts 40 by heating 42 a mouthpiece body 22 made of a thermoplastic material and having a shape generally complementary to the person's dental arch. The mouthpiece body 22 includes a posterior end 24 having two spaced apart members 26 positioned toward the back of the person's dental arch when properly worn, and an anterior end 28 having an airway opening 30 therethrough, the anterior end positioned when properly worn to support the person's lips spaced apart so that air flows through the opening. The mouthpiece 20 further includes a substantially rigid portion or protective mold 32 made of a thermostable material, the protective mold being complementary to the thermoplastic portion of the mouthpiece body. The protective mold portion 32 is an integral, unitary piece with the mouthpiece body portion 22 so that the mold protects at least lower and preferably also lateral peripheries of the thermoplastic portion. Heating 42 of the mouthpiece body is preferably accomplished in a hot water bath and continues until the thermoplastic material has softened. When the mouthpiece 20 is cool enough, the method continues by inserting 44 the mouthpiece into the mouth of a person so that the thermoplastic mouthpiece portion is substantially aligned with the person's dental arch, and imprinting 46 the person's teeth along a surface of the thermoplastic mouthpiece portion not protected by the thermostable mold portion 32 by biting down on the mouthpiece. In an embodiment of the method, the user preferably picks up the mouthpiece by the removable plug 33 when heating it and when inserting it into the user's mouth, thereafter removing the plug to leave an unobstructed airway opening. Finally, the method calls for wearing 48 the mouthpiece body 22 in the person's mouth during sleep, which when properly positioned the mouthpiece is substantially aligned with the person's dental arch and is held between the teeth, so that the person's lips are supported by the anterior end 28 of the mouthpiece body 22 to allow the person to breathe through the airway opening 30 in the anterior end of the mouthpiece body. The method thereafter ends 50.

Those skilled in the art should understand that the thermostable protective mold portion 32 being integral with the thermoplastic mouthpiece body portion 22 will prevent teeth from imprinting along the lower surface 34 of the thermoplastic mouthpiece, thereby maintaining the lower surface relatively flat. The wearer's teeth will, however, imprint along the upper thermoplastic surface 38 of the mouthpiece, so as to provide a guide pattern for wearing the mouthpiece and to reduce slipping of the mouthpiece body 22 in the wearer's mouth. The relatively flat lower surface 34 of the mouthpiece body 22 helps in maintaining angle "α" in proper proportion, as it has been found that if the wearer imprints teeth along both upper 38 and lower 34 surfaces by biting down thereon, the angle "α" tends to be substantially reduced due to the depressions formed along both upper and lower surfaces of the mouthpiece. Imprinting teeth along only one surface reduces this possible variation at least in half, while still producing an easily wearable mouthpiece custom fitted to the wearer's dental arch. In addition, in a user who tends to grind his/her teeth while sleeping, the relatively flat lower surface 34 of the mouthpiece body 22 will allow the teeth to more easily slide relative to the mouthpiece surface. If the lower surface 34 contained teeth imprints, the user's teeth would be substantially locked into their positions and a user grinding her teeth during sleep would experience added stress to the temporal-mandibular joint (also known as TMJ). Accordingly, the relatively flat lower surface of the present mouthpiece will also help alleviate such stress in the TMJ and neck area.

The skilled will readily understand that while the thermostable protective mold portion 32 has been described herein with respect to a lower surface 34 of the mouthpiece body 22, and imprinting has been described as occurring along the upper surface 38 of the mouthpiece, the wearer may prefer to turn the mouthpiece device upside down for imprinting. In such a case, the protective mold 32 would appear to engage an upper surface of the mouthpiece, and the teeth pattern would be imprinted along what might be described as a lower surface of the mouthpiece. Accordingly, the terms "upper" and "lower" are used herein to illustrate the invention for the skilled and are not intended to limit the invention to such an orientation. The inventive mouthpiece herein described is, therefore, usable in any applicable orientation, at the user's discretion or preference.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A mouthpiece for use by a person during sleep to aid in reducing snoring, said mouthpiece comprising:
    a mouthpiece body of a thermoplastic material having a shape generally complementary to the person's dental arch, including a posterior end having two spaced apart members positioned toward the back of the person's dental arch when properly worn, and an anterior end having an airway opening therethrough, the anterior end positioned when properly worn to support the person's lips spaced apart so that air flows through the airway opening;
    a plate member comprising material extending between said two spaced apart members from approximately the posterior end to the anterior end of said mouthpiece body; and
    a substantially rigid, protective mold of a thermostable material, said protective mold forming a portion of said mouthpiece body so that the mold protects at least a periphery of the mouthpiece body from imprinting by teeth.

2. The mouthpiece of claim 1, wherein said plate member comprises thermoplastic material.

3. The mouthpiece of claim 1, wherein said plate member comprises thermostable material.

4. The mouthpiece of claim 1, wherein said mouthpiece body and said mold comprise two separable pieces.

5. The mouthpiece of claim 1, wherein said mouthpiece body and said mold comprise a single non separable piece.

6. The mouthpiece of claim 1, wherein the airway opening comprises a thermostable material.

7. The mouthpiece of claim 1, wherein said mouthpiece body has a lower surface and an upper surface spaced apart therefrom at an angle which increases from the posterior end to the anterior end of said body.

8. A mouthpiece for use by a person during sleep to aid in reducing snoring, said mouthpiece comprising:
    a mouthpiece body of a thermoplastic material having a shape generally complementary to the person's dental arch, including a posterior end having two spaced apart members positioned toward the back of the person's dental arch when property worn, and an anterior end, the anterior end positioned when properly worn to support the person's lips spaced apart so that air flows through the airway opening;
    an airway comprising a hollow member projecting outwardly from said anterior end, said hollow member having an airway opening therethrough;
    a plate member comprising material extending between said two spaced apart members from approximately the posterior end to the anterior end of said mouthpiece body; and
    a substantially rigid, protective mold of a thermostable material, said protective mold forming a portion of said mouthpiece body so that the mold protects at least a periphery of the mouthpiece body from imprinting by teeth.

9. The mouthpiece of claim 8, wherein said mouthpiece body has a lower surface and an upper surface spaced apart therefrom at an angle which increases from the posterior end to the anterior end of said body.

10. The mouthpiece of claim 8, further comprising a removable plug inserted in the airway opening and protruding therefrom.

11. The mouthpiece of claim 8, wherein said plate member comprises thermoplastic material.

12. The mouthpiece of claim 8, wherein said plate member comprises thermostable material.

13. The mouthpiece of claim 8, wherein said mouthpiece body and said mold comprise two separable pieces.

14. The mouthpiece of claim 8, wherein said mouthpiece body and said mold comprise a single non separable piece.

15. The mouthpiece of claim 8, wherein the airway opening comprises a thermostable material.

* * * * *